US009267181B2

(12) United States Patent
Dhepe et al.

(10) Patent No.: US 9,267,181 B2
(45) Date of Patent: Feb. 23, 2016

(54) ONE POT AND SINGLE STEP HYDROLYTIC PROCESS FOR THE CONVERSION OF LIGNOCELLULOSE INTO VALUE ADDED CHEMICALS

(75) Inventors: Paresh Laxmikant Dhepe, Maharashtra (IN); Ramakanta Sahu, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 995 days.

(21) Appl. No.: 13/500,131

(22) PCT Filed: Jan. 27, 2010

(86) PCT No.: PCT/IN2010/000047

§ 371 (c)(1),
(2), (4) Date: Apr. 4, 2012

(87) PCT Pub. No.: WO2011/092711

PCT Pub. Date: Aug. 4, 2011

(65) Prior Publication Data

US 2012/0192860 A1 Aug. 2, 2012

(51) Int. Cl.
*C07C 37/54* (2006.01)
*C13K 13/00* (2006.01)

(52) U.S. Cl.
CPC ............... *C13K 13/002* (2013.01); *C13K 13/00* (2013.01)

(58) Field of Classification Search
None
See application file for complete search history.

(56) References Cited

U.S. PATENT DOCUMENTS

| | | | | |
|---|---|---|---|---|
| 5,457,078 | A * | 10/1995 | Absil et al. | 502/68 |
| 6,100,385 | A * | 8/2000 | Naae et al. | 530/502 |
| 7,084,293 | B2 * | 8/2006 | Rosier et al. | 558/335 |
| 2008/0050792 | A1 * | 2/2008 | Zmierczak et al. | 435/161 |
| 2009/0118494 | A1 * | 5/2009 | Blair et al. | 536/127 |
| 2010/0307050 | A1 * | 12/2010 | Sen et al. | 44/352 |

OTHER PUBLICATIONS

Antonakou et al, Evaluation of various types of Al-MCM-41 materials as catalysts in biomass pyrolysis for the production of bio-fuels and chemicals, 2006, fuel, 85, pp. 2202-2212.*
Binder et al, Reactions of lignin model compounds in ionic liquids, 2009, biomass and bioenergy, 33, pp. 1122-1130.*

* cited by examiner

*Primary Examiner* — Melvin C Mayes
*Assistant Examiner* — Stefanie Cohen
(74) *Attorney, Agent, or Firm* — Ladas & Parry LLP

(57) ABSTRACT

The present invention provides a single step hydrolytic process for the conversion of lignocellulose, into value added chemicals wherein said process is catalyzed by at least one heterogeneous solid acid catalyst selected from a group comprising of zeolites, zeolites with Si/metal, mesoporous silica, oxides and phosphates, clays, ion-exchange resins, heteropolyacids, various sulfates, phosphates, selenates, crystalline materials and amorphous materials.

3 Claims, 5 Drawing Sheets

ONE POT AND SINGLE STEP HYDROLYTIC PROCESS FOR THE CONVERSION OF LIGNOCELLULOSE INTO VALUE ADDED CHEMICALS

RELATED APPLICATION INFORMATION

This application is a 371 of International Application PCT/IN2010/000047 filed 27 Jan. 2010 entitled "A ONE POT AND SINGLE STEP HYDROLYTIC PROCESS FOR THE CONVERSION OF LIGNOCELLULOSE INTO VALUE ADDED CHEMICALS", which was published in the English language on 4 Aug. 2011, with International Publication Number WO 2011/092711 A1, the content of which is incorporated herein by reference.

FIELD OF INVENTION

The present invention relates to a single step hydrolytic process for the conversion of lignocellulose into value added chemicals. More particularly, the present invention relates to a single step hydrolytic process for the conversion of a non-edible source such as hemicellulose to value added chemicals such as arabinose and xylose catalyzed by a heterogenous catalyst.

BACKGROUND OF THE INVENTION

Lignocelluloses are available in plentiful and is a renewable resource made up of ca. 40-50% cellulose, 25-30% hemicellulose and 20-25% lignin. Technologies are in place to separate cellulose, hemicellulose and lignin from each other and hence raw material, hemicellulose is readily available.

Hemicellulose a carbohydrate is abundantly and cheaply available across the globe and is a main factor that many countries will be independent about their chemical needs. Hemicellulose, which is basically derived from the non-edible source, will have advantage over edible sources for their conversion into chemicals as it is independent of food-crisis and geo-political factors.

Conversion of fossil feedstock (crude oil, natural gas, coal etc.) into chemicals and energy produces significant amount of carbon dioxide which causes global warming. The recent exponential price rise of crude oil on the back-drop of mismatch in increasing demand and limited supply has pushed the world economy to a jinx. Moreover, geo-political factors and finite reserves available in only selective areas on the earth are also held responsible for the current situation. To maintain the prices of fuels and to keep carbon dioxide at constant levels, efforts are being made in the field of production of biomass based fuels (bio-ethanol and bio-diesel) and this in turn has made the whole situation more complex. As these fuels are mostly sought from the increasing uses of edible sources such as starch (corn, rice etc.) and vegetable oils (seed oils), it has attracted a lot of criticism across the globe on the note of increasing food prices. Thus, ways to overcome limitations arising from the use of fossil feedstock and edible sources for the synthesis of chemicals are being sought by way of the utilization of non-edible biomass resource under the bio-refinery title. Biomass during its growth captures light energy, water and carbon dioxide to form carbohydrates in a photosynthesis process. The integral part of fixing of $CO_2$ during carbohydrate synthesis makes the utilization of plant derived biomass a totally "carbon neutral" process. The net annual yield of photosynthesis is around 1.3 trillion tons, thus making it the largest renewable resource available and a part of this renewable, non-edible resources are lignocellulosic materials such as wood and agricultural wastes.

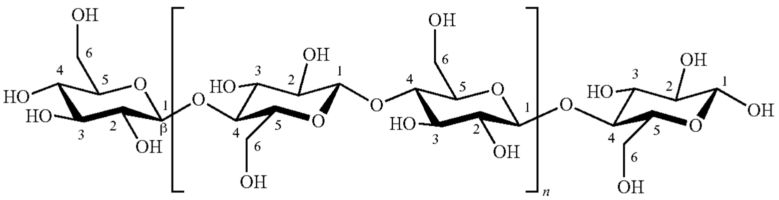

β-(1 → 4) linkage

Structure of Cellulose

While, the main component of wood is cellulose, which constitutes almost 40-50% of wood material, the other major constituent (ca. 25-30%) of wood and second largest renewable feedstock derived from plant is hemicellulose. Cellulose is made up of C6 (hexoses) glucose units and is a highly crystalline material. On the other hand hemicelluloses are complex heterogeneous polymers composed of largely C5 (D-pentoses) and C6 (D-hexoses) monosaccharides such as, Xylose, Mannose, Arabinose, Glucose, Galactose, Glucuronic Acid Uronic Acid etc. depending on the source, as disclosed in the figure herein below. The softwood hemicellulose mainly consists of Xylose, Arabinose, Mannose, Galactose, Glucuronic Acid etc. and hardwood hemicellulose are mainly made up of Xylose and Glucuronic Acid. Concluding from the above discussion, there are 4 major factors, namely food security, cost efficiency, climate change and localized industry independent of geopolitical scenarios, which are driving the global research community to work on non-edible renewable sources for chemical and fuel production.

Softwood Derived Hemicellulose

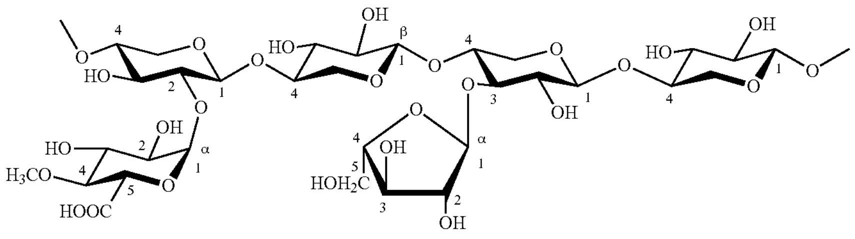

4-O-methyl-D-glucuronic acid
α-(1 → 2) bonds

L-arabinose
α-(1 → 3) bonds

Hardwood Derived Hemicellulose

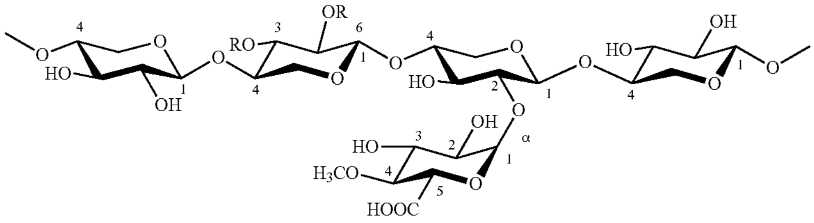

4-O-methyl-D-glucuronic acid
α-(1 → 2) bonds

To convert lignocellulosic material (cellulose, hemicellulose and lignin) into chemicals and fuels, these polysaccharides must be selectively decomposed into corresponding monosaccharides. Currently, lot of research is devoted to the hydrolysis (or decomposition) of the lignocellulosic materials into value-added chemicals. The known technologies for biomass hydrolysis include, dilute acid hydrolysis, concentrated acid hydrolysis, alkaline hydrolysis and enzymatic hydrolysis. In the hydrolysis process, in the presence of excess water, the ketal function of the polysccharides can be hydrolyzed to form hemi-acetals and this could liberate monomer form of sugars via oligomer formation. Being water insoluble, hydrolysis of cellulose and hemicellulose is a difficult task and hence requires specific reaction conditions.

Acid hydrolysis (either dilute or concentrated HCl, $H_2SO_4$) of hemicellulose is known for quite a long time but due to difficulty in inhibition of xylose degradation, corrosion hazard, problems in handling and, storage of acids and generation of neutralization waste, its industrial use is hampered. In the older times, concentrated inorganic acids ($H_2SO_4$) under milder conditions (100-150° C.) were used, but the recovery of acids was very difficult and was expensive. To overcome this, later dilute acid pathway was established, but required severe conditions such as 150-200° C. and positive pressure.

The other widely studied method for hydrolysis of lignocellulosic materials is enzyme catalyzed reactions. For hydrolysis of hemicellulose, mixture of endo-, exo-Xylanase and β-Xylosidase is used additionally with α-Arabinofuranosidase and some other enzymes. The enzymatic hydrolysis which is very specific towards product formation is normally done at lower temperatures (50-80° C.) but at definite pH (acidic). The known drawbacks of this method are low activity, use of buffers to maintain a specific pH at which enzymes work and make the system corrosive and high cost of enzymes that hampers cost efficiency and also, product-enzyme separation is difficult as both product and catalyst are water soluble.

Thermochemically (>700° C.) also, degradation of ligoncellulosic materials is possible. In the gasification process, lignocellulosic material is decomposed at high temperatures under restricted oxygen to give valuable syngas ($CO+H_2$). Several such processes are known. In the pyrolysis method, without oxygen lignocellulosic material is heated at high temperatures to yield mixture of oils, tar and char. In these processes it is difficult to obtain high selectivity for any one compound due to very high temperatures employed under which normal sugars are unstable and undergo further decompositions. The other drawback is formation of char, tar and oils. These compounds don't have much market value due to their complex structures and thus might be considered as a waste. Lastly these methods require very high energy input and so are not cost-effective.

Hydrolysis of lignocellulosic materials using hot-compressed water (sub and supercritical waters) is also reported. In this technique in the absence of catalyst at 200-380° C. and about 22 MPa, lignocellulosic material is subjected to critical water condition for short period of time to form hydrolysis products. Lack of high selectivity for any product due to further reaction (towards decomposition) and requirement of high energy input restricts its use. Additionally, under these conditions, water becomes super acidic and hence can corrode the reactor material which increases the capital cost of the whole process.

A research paper published in Energy and Fuels 2005, titled, "Plug-Flow reactor for continuous hydrolysis of Glucans and Xylans from pretreated corn fiber" by Young Mi Kim, Nathan Mosier, Rick Hendrickson and Michael R. Ladisch; Vol. 19, pages 2189-2200 discloses the use of solid strong acid catalyst in the form of solid ion-exchange resins (Amberlyst 35W resin micro reticular type; Dowex 50WX2, SK104, SK110 gel type) packed in fixed-beds at 130° C. for continuous hydrolysis of soluble Glucans and Xylans. It is also disclosed that first insoluble hemicelluloses is under 160° C., and pH 4-7 is converted into soluble form (oligosaccharides) and then these disslolved oligosaccharides are separated out by centrifugation and are further exposed to ion-exchange resins. The reaction is a two step process.

Another research paper published in Angewandte Chemie Int. Ed. titled "Catalytic conversion of cellulose into sugar alcohols" by Atsushi Fukuoka and Paresh L. Dhepe; 2006, 45, 5161-5163; related to the hydrolysis of cellulose to glucose and the reduction of glucose to sorbitol and mannitol by the use of metal catalyst supported over material selected from the group of gamma-$Al_2O_3$, HY (2.6), HUSY (15), HUSY (20), HUSY (40), HZSM-5 $SiO_2$—$Al_2O_3$, $SiO_2$, $TiO_2$, $ZrO_2$, FSM-16, H-Beta, HMOR or activated carbon.

WO2007/100052 A1 titled "Catalyst for hydrolysis of cellulose and/or reduction of hydrolysis product thereof; and method for producing sugar alcohol from cellulose discloses hydrolysis of a cellulose and/or reduction of hydrolysis product thereof, in the presence of a catalyst, selected from the periodic group of 8-11 transition metal (Pt, Ru, Pd, Rh, Ni, Ir).

Further, EP0329923 discloses production of polyhydric alcohol from polysaccharide (starch) using metal supported over silica-alumina or solid acidic catalyst from the group of acidic zeolite (Faujasite type zeolite, HZSM-5, H-Beta, H-Modernite).

U.S. Pat. No. 4,075,406 titled "Process for making Xylose" describes a method for recovering xylose from pentosan, preferably Xylan-containing raw materials including the steps of sulfuric acid hydrolysis of the raw material, purifying the hydrolysate by ion exclusion and color removal and then subjecting the purified solution to chromatographic fractionation on an ion exchange resin column to provide a solution containing a high level of Xylose.

Taking clue from the above discussed technologies and their limitations, study on hemicellulose hydrolysis catalyzed by solid acids was taken up. The major advantages of using solid acids being, ease of separation of catalyst (solid) and product (water soluble) by simple filtration and working under neutral conditions without any corrosion (as acid sites are bound to solid and are not liberated out in the reaction media) in a totally green environment (as no neutralization waste would be generated and water is used as a reaction media).

None of the prior art disclosed above teaches or explains a cost-effective, anti-corrosive, one-pot reaction of hydrolysis of hemicellulose.

OBJECTS OF THE INVENTION

The main object of the present invention is to provide a one step process for conversion of a non-edible source such as lignocellulose to a value added material such as Xylose, Arabinose, glucose, Mannose, glucuronic acid, furaldehyde etc.

Yet another object of the invention is to provide a single step hydrolysis of lignocellulose to Xylose and arabinose catalyzed by solid heterogenous acid catalyst.

SUMMARY OF THE INVENTION

Accordingly the present invention provides one pot and a single step hydrolytic process for the conversion of lignocellulose into value added chemicals, the said process comprising the steps of:

a. charging the lignocellulose in the reactor followed by charging a solvent and at least one heterogeneous solid acid catalyst;
b. optionally flushing the reactor with inert gas or air;
c. adjusting the pressure to 1-70 bar and temperature of 50-250° C. of the reactor, under stirring;
d. raising the stirring speed to 10-2000 rpm after stabilizing the required temperature;
e. carrying the above said reaction for a period of 0.1 to 96 hours to obtain the desired value added product.

In an embodiment of the present invention the heterogeneous solid acid catalyst used is selected from the group comprising of zeolites, zeolites with Si/metal, mesoporous silica, oxides and phosphates, clays, ion-exchange resins, heteropolyacids, various sulfates, phosphates, selenates, crystalline materials and amorphous materials.

In yet another embodiment the catalyst used is zeolite catalyst with Si/Al=1-100 with regular pore structure and pore diameter in the range of 0.3-1.5 nm, zeolites such as, ZSM-5, Y, X, Beta and MOR, zeolites in their H form, Na or $NH_4$ forms, but are converted into H form to generate acidic sites.

In yet another embodiment the catalyst zeolites with Si/Metal used are zeolites with a ratio of Si to Metal=1-100 (metallosilicates), wherein metal is Ga, Ti, Fe, Cr, Zn, P, B, or Zr.

In yet another embodiment the catalyst used is mesoporous silica catalyst selected from MCM-41, FSM-16, SBA-15, HMM type with regular pore structure and >2 nm pore diameter and silicas with functional groups attached such as carboxylic acid, thiol, —$SO_3$H.

In yet another embodiment the mesoporous silica catalysts used are optionally incorporated with metal selected from Ga, Al, Sb, In, Fe, Ti, and P.

In yet another embodiment the mesoporous silica catalyst used is selected from Al-MCM-41, Al-SBA-15 and Ga-MCM-41.

In yet another embodiment the oxide and phosphate catalysts used is selected from the group consisting of Niobic acid ($Nb_2O_5$), $MoO_3/ZrO_2$, $WO_3/ZrO_2$, Zirconium phosphates, Lanthanum phosphates, Niobium phosphates and Mo, W, Nb, P, V, Si, Al supported on or mixed with $SiO_2$, $Al_2O_3$, $SiO_2$—$Al_2O_3$, $TiO_2$, C, metal oxides, polymers, and supports either alone or in combinations thereof.

In yet another embodiment the clay catalyst used is selected from the group consisting of aluminosilicates, phyllosilicates, pillared clays, cation exchanged clays and acid treated clays, preferably Montmorillonite (K10) type.

In yet another embodiment the ion-exchange resins catalyst used is preferably cation exchangers selected from the group consisting of Amberlyst-15, Amberlyst-35, Amberlite, Amberjet, Aowex, Auolite, Nafion beads (NR50 type) and nafion-silica composites (SAC-13 type) types.

In yet another embodiment the hetero polyacid catalyst used is selected from the group consisting of Keggin type, Dawson type, Waugh type, Anderson type and Silverton type.

In yet another embodiment the heteropoly acid catalyst used is optionally phosphotungstic acid, phosphomolybdic acid, silicotungstic acid and molybdovanadophosphoric heteropolyacids or the anions thereof, supported on the group comprising of metal oxides, carbon, resins, polymers and/or the metal replacing $H^+$ such as $Cs_xH_{3-x}PW_{12}O_{40}$, where x=0-3 and $Cs_xH_{4-x}SiW_{12}O_{40}$, where x=0-4 type. The replacement metal can be Cs, Pd, Rh and such like.

In yet another embodiment the heterogeneous catalyst used is selected from sulphates, phosphates and selenates.

In yet another embodiment the supports used are optionally crystalline or amorphous selected from the group consisting of $Al_2O_3$, $ZrO_2$, $SiO_2$, $TiO_2$, organo-silicates, carbon, polymers, oxides as such or modified with acid treatment or functionalized to give acidic properties.

In yet another embodiment the inert gas used in step b is selected from nitrogen, argon, helium and hydrogen.

In yet another embodiment the substrate to solvent ratio used is in the range of 0.001-0.5 wt/wt.

In yet another embodiment the substrate to catalyst ratio used is in the range of 0.2-500 wt/wt.

In yet another embodiment the solvent used in the reaction is either organic solvent or a mixture of water and organic solvent in an ration of 1:99 to 99:1 and organic solvent is selected from the group consisting of alcohols, ethers, esters, hexane, acids, toluene, and xylene.

In yet another embodiment the catalyst used is recyclable and reusable.

In yet another embodiment the source of hemicelluloses used is selected from the group consisting of softwood, hardwood, lignocelluloses, grasses, crops, spent crops, trees, plants, wood residues, agricultural wastes, forest residues, pulp, paper, pulp and paper waste, municipal waste, food processing waste and by-products thereof.

The present invention relates to a one step process of hydrolysis of lignocellulose to Xylose and arabinose catalyzed by solid heterogenous acid catalyst. Hemicellulose (model substrate Xylan) is derived from either oat spelt or birchwood which is charged in the reactor. Water and catalyst are also charged and then reactor is flushed with nitrogen and final pressure of 1-70 bar is maintained at room temperature. Reactor is heated up to desired temperature (50-250° C.) under slow stirring. Once the desired temperature is attained, stirring is increased to 500 rpm. Reactions are done for varying time period of 0.1 to 96 hours.

DETAILED DESCRIPTION OF THE INVENTION

Figure 1:
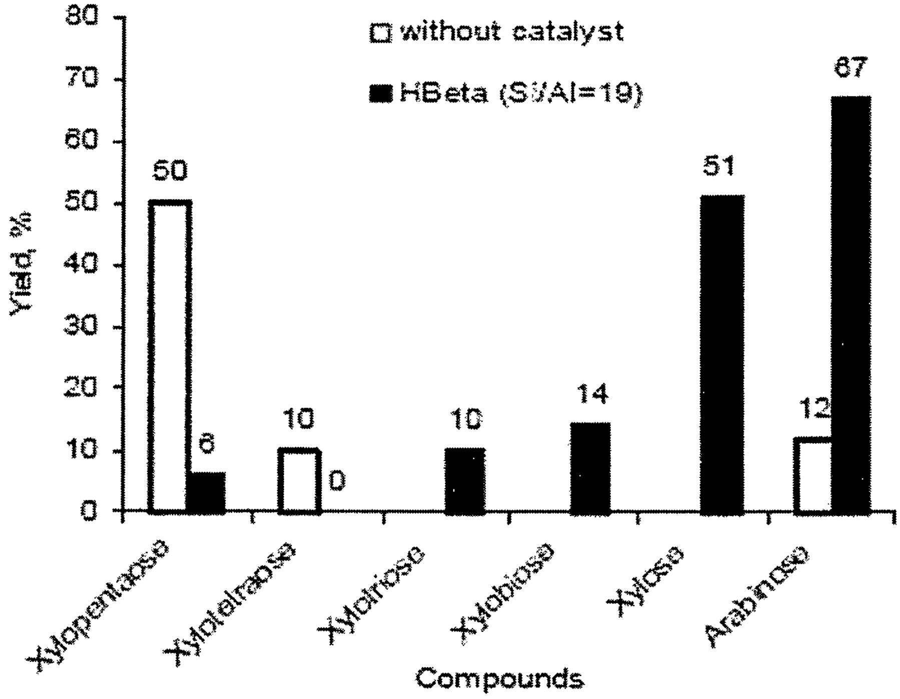
FIG. 1 illustrates Effect of catalyst on hydrolysis of hemicellulose: Xylan (oat spelt), 0.6 g; catalyst, 0.3 g; water, 60 g; $N_2$ pressure, 50 bar at RT; temperature, 130° C.; reaction time, 48 h; stirring, 500 rpm.

The present invention disclosed herein describes a novel, one step environmentally benign process for conversion by hydrolysis of a non-edible material, such as lignocellulose into value added, materials such as xylose, arabinose, glucose, mannose, galactose, glucuronic acid and such like wherein such process of hydrolysis is catalyzed by a heterogeneous, solid acid catalyst. Lignocellulosic material or lignocellulose of the invention is cellulose, hemicellulose and lignin.

The substrate for the reaction is hemicellulose embedded in the cell walls of any plant, and can be derived from any softwood or hardwood source and is insoluble in water. Softwood hemicelluloses are derived from plants such as, pine, spruce, cedar, fir, larch, douglas-fir, hemlock, cypress, redwood, yew, red deal, yellow deal, western red and such like. Hardwood hemicelluloses are derived from plants such as, european english oak, beech, ash, elm, sycamore, birch, walnut and such like. Other sources of hemicelluloses can be selected from lignocelluloses and grasses, crops, spent crops, trees, plants, wood residues (including saw mill waste), agricultural wastes (including corn stover, bagasse), forest residues, pulp and paper and their waste, municipal waste, food processing waste and by-products etc.

The reaction is conducted in a reactor type which is selected from autoclave, stainless steel vessel or teflon vessels or glass reactor or plate plasma type reactor with varying capacity.

The reaction is carried out at temperature ranging from 50° C. to 250° C., under inert gas (nitrogen, helium, argon etc.) or hydrogen or air pressure of 0.1-70 bar. The reaction time varies from 0.1-96 hours at 10-2000 rpm speed with optional flushing.

The solvent for the reaction is selected from the group comprising combinations of water and organic solvents in the ratio of 1:99 to 99:1. The organic solvent comprises the group of alcohols, ethers, hexane, toluene, xylene and such like.

The substrate: solvent ratio varies in the range of 0.001-0.5 wt/wt.

The substrate: catalyst concentration of the invention is in the range of 0.2-500 wt/wt.

In an embodiment of the invention, hemicellulose, model substrate xylan derived from oat spelt or birchwood is charged in the reactor. Water and catalyst are charged and reactor is flushed with nitrogen and final pressure of 1-70 bar is maintained at room temperature. Reactor is heated up to desired temperature (50-250° C.) under slow stirring. Stirring is increased to 500 rpm and reaction is carried out for 0.1-96 hours to obtain xylose, arabinose and glucose and xylitol. Further the reaction mixture is analyzed by HPLC/LC-MS and yield is determined.

The heterogenoues catalysts of the instant invention are selected from the solid acid catalyst group comprising of zeolites, zeolites with Si/metal (metallosilicates), mesoporous silica, modified mesoporous silicas, oxides and phosphates, clays, ion-exchange resins, heteropolyacids, various sulfates, phosphates, selenates, crystalline materials, amorphous materials and such like. Catalyst can be from rare earth element and its compounds either supported as acidic or neutral support or are in combination with sulfates or its precursor. Catalysts are optionally activated either at 150° C. or at 550° C. for 1-16 hours in air or under vacuum. Further the catalyst of the invention can be reused as exemplified herein below.

The zeolites with Si/Al=1-100 with regular pore structure and pore diameter in the range of 0.3-1.5 nm including zeolites such as, ZSM-5, Y, X, Beta, MOR and such like, in their H form or in Na or $NH_4$ forms, but before reaction are converted into H form to generate acidic sites, are the zeloite class of catalyst of the instant invention.

Zeolites with Si/Metal=1-100 (metallosilicates), wherein metal is Ga, Ti, Fe, Cr, Zn, P, B, or Zr can also catalyze the hydrolytic conversion of hemicellulose. Metal can also be from rare earth metals.

The solid acids can also be selected from various mixed metals such as silicaaluminophosphates (SAPO), ALPO and such like.

The mesoporous silica catalysts are MCM-41, FSM-16, SBA-15, HMM type with regular pore structure and >2 nm pore diameter, including said silicas with functional groups attached such as carboxylic acid, thiol, —$SO_3H$ and such like.

The mesoporus silicas with metal incorporated to increase the acidity are such as Al-MCM-41, Ga-MCM-41, Al-SBA-15 and such like. The oxide and phosphate catalysts that catalyse hydrolysis of hemicelluloses are Niobic acid ($Nb_2O_5$), $MoO_3/ZrO_2$, $WO_3/ZrO_2$, Zirconium phosphates, Lanthanum phosphates, Niobium phosphates and Mo, W, Nb oxides supported on $SiO_2$, $Al_2O_3$, $SiO_2$—$Al_2O_3$ and such like. The clay catalysts of the invention are selected from aluminosilicates, phyllosilicates, pillared clays, cation exchanged clays, acid treated clays, preferably Montmorillonite (K10) type.

Ion-exchange resins, preferably cation exchangers selected from Amberlyst-15, Amberlyst-35, Amberlite, Amberjet, Dowex, Duolite, Nafion beads (NR50 type) and Nafion-silica composites (SAC-13 type) can catalyze reaction of instant invention.

The heteropolyacids are selected from Keggin type, Dawson type, Waugh type, Anderson type or Silverton type. Heteropoly acid is optionally phosphotungstic acid, phosphomolybdic acid, silicotungstic acid or molybdovanadophosphoric heteropolyacids or the anions thereof. They are supported catalysts wherein said support is selected from the group consisting of metal oxides, carbon, resins and polymers. The metal replacing $H^+$ are also included such as $Cs_xH_{3-x}PW_{12}O_{40}$, where x=0-3.

Other catalysts of the invention are various sulfates, phosphates, selenates and various supports that are optionally either crystalline or amorphous selected from, $Al_2O_3$, $ZrO_2$, $SiO_2$, $TiO_2$, organo-silicates, carbon, sulphated zirconia, polymers, oxides as such or modified with acid treatment. The mixed metal oxides such as $Cu/ZnO/Al_2O_3$ and such like.

In one embodiment of the invention, the single step hydrolytic process as described herein further comprised the conversion of cellulose to value added derivative products selected from xylose, arabinose, xylitol, arabitol, furfural, xylaric acid, glycols and hydroxy furans. The step of conversion of cellulose to value added derivative products is catalyzed by solid acid catalysts and supported metal catalysts. The processes of conversion of hemicellulose and cellulose to value added deriviative products are a single pot processes.

As observed in the Figural, formation of xylose from hemicellulose requires a catalyst, with more than 90% conversion and 51% xylose yield is obtained on HBeta (Si/Al=19) catalyst with reaction conditions mentioned in the FIG. 1. Besides xylose formation, oligomers such as, xylopentaose (5 units of xylose linked with each other), xylotriose (3 units of xylose linked with each other) and xylobiose (2 units of xylose linked with each other) are also obtained with yields of 6, 10 and 14%, respectively. Without catalyst only 50% xylopentaose and 10% xylotetraose (4 units of xylose linked with each other) yield is observed and no xylose formation was possible. This clearly emphasize the fact that the hemicellulose hydrolysis reaction is a catalytic reaction i.e. reaction requires acid catalyst. The formation of glucose is not observed because of overlapping of glucose and xylose peaks in the analysis. However, calculations for xylose formation are based on combined area (glucose+xylose) and total xylose and glucose present in the substrate (i.e. in model substrate of oat spelt, ≥70% xylose and ≤15% glucose is present).

Figure 2:
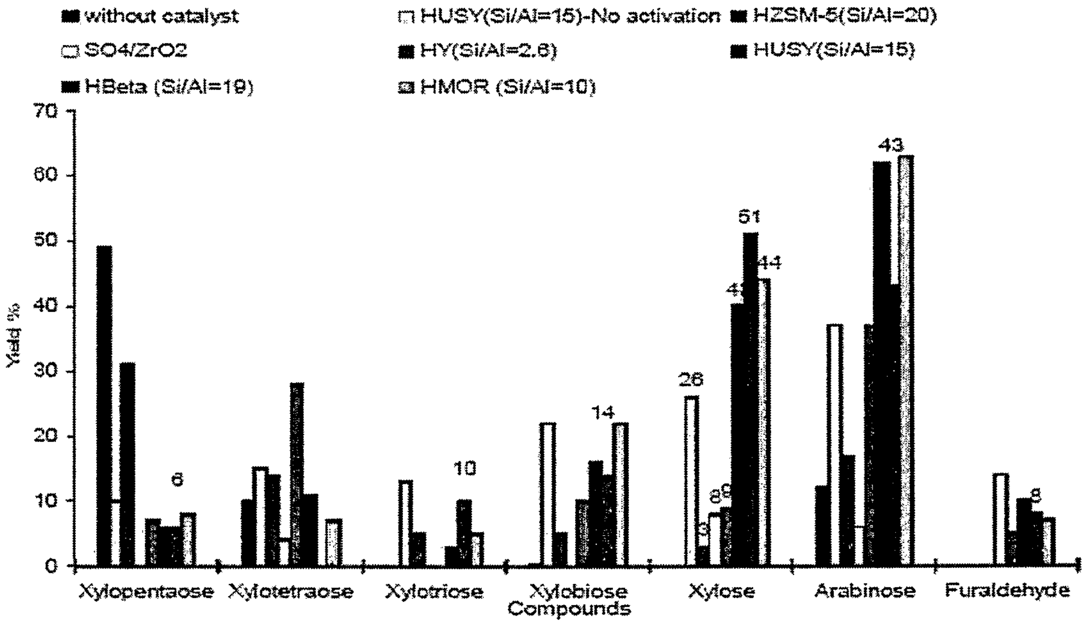
FIG. 2 illustrates solid acid catalyzed hydrolysis of hemicellulose: Xylan (oat spelt), 0.6 g; catalyst, 0.3 g; water, 60 g; $N_2$ pressure, 50 bar at RT; temperature, 130° C.; reaction time, 48 h; stirring, 500 rpm.

As seen in FIG. 2, it is observed that during the course of the reaction, first hemicellulose is thermally decomposed to oligomers, which in turn are converted further into monomer (xylose). It is also interesting to note that, after activation of the HUSY (Si/Al=15) catalyst, xylose yield (40%) increases compared with non-activated catalyst (26%). Arabinose formation was also seen with yield of ca. 70%. Formation of furaldehyde derived from the dehydrocyclization of xylose and/or arabinose was also observed with yield of 14% on $SO_4^{2-}/ZrO_2$ catalyst.

Figure 3:
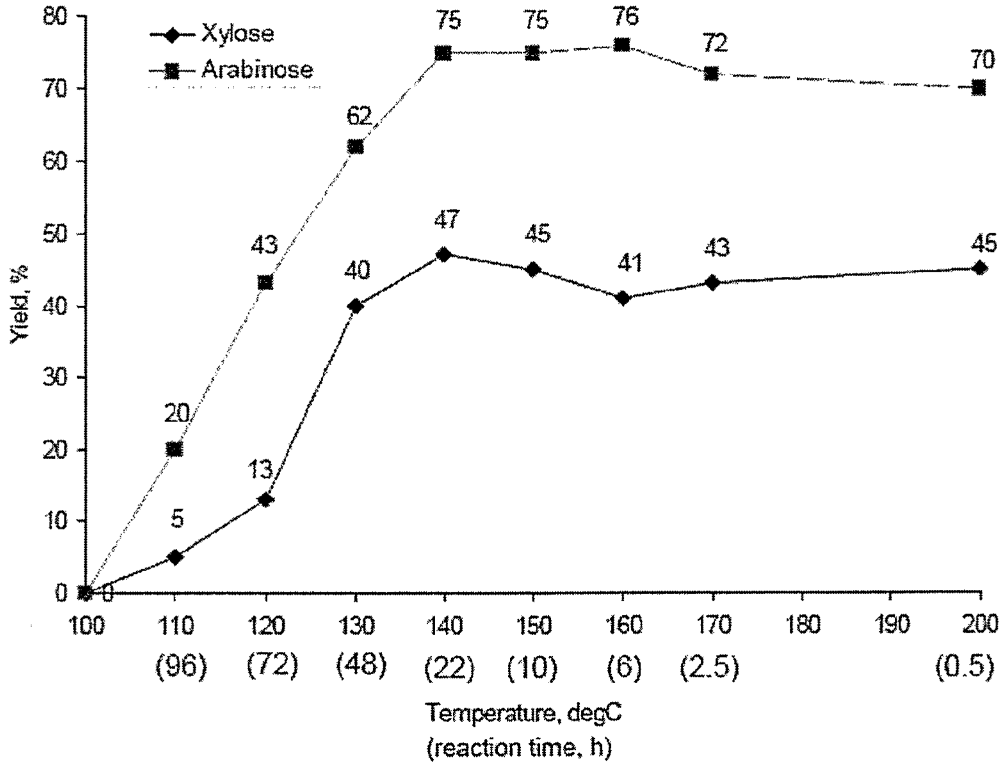
FIG. 3 illustrates effect of temperature on hemicellulose hydrolysis: Xylan (oat spelt), 0.6 g; HUSY (Si/Al=15), 0.3 g; water, 60 g; $N_2$ pressure, 50 bar at RT; stirring, 500 rpm.

The effect of temperature on the catalytic reaction of instant invention is seen in FIG. 3. It is clearly seen that the reaction is very much dependent on temperature. At 100° C., about no xylose formation is observed but as temperature increases from 100 to 200° C., formation of xylose increases with decrease in time. At 120° C., 13% of xylose formation is observed after 72 h reaction time, whereas at 130 and 140° C., 40 and 47% of Xylose formation is observed after 48 and 22 h reaction time, respectively. If temperature is further increased to 150° C., 160° C. and 170° C., xylose formation is at, 45, 41, 43% after 10, 6 and 2.5 h time, respectively. Further increase in temperature to 200° C., gave 45% xylose within 30 min of reaction time.

Figure 4:
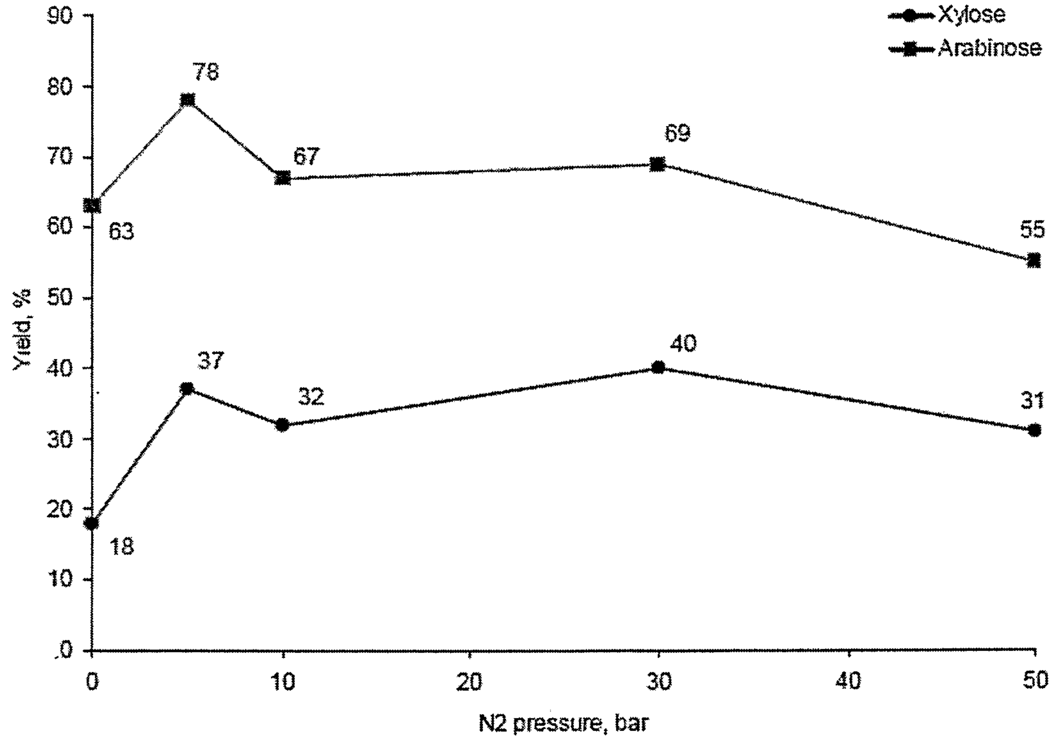
FIG. 4 illustrates effect of pressure on hemicellulose hydrolysis: Xylan (oat spelt), 0.6 g; HUSY (Si/Al=15), 0.3 g; water, 60 g; temperature 130° C.; reaction time, 24 h; stirring, 500 rpm.

It is observed from FIG. 4 that at 1 atm pressure, after 24 h reaction with HUSY (Si/Al=15) catalyst, 18% xylose is formed. As pressure increased to 5 bar and above, xylose formation almost remains constant (ca. 30-40%).

Figure 5:
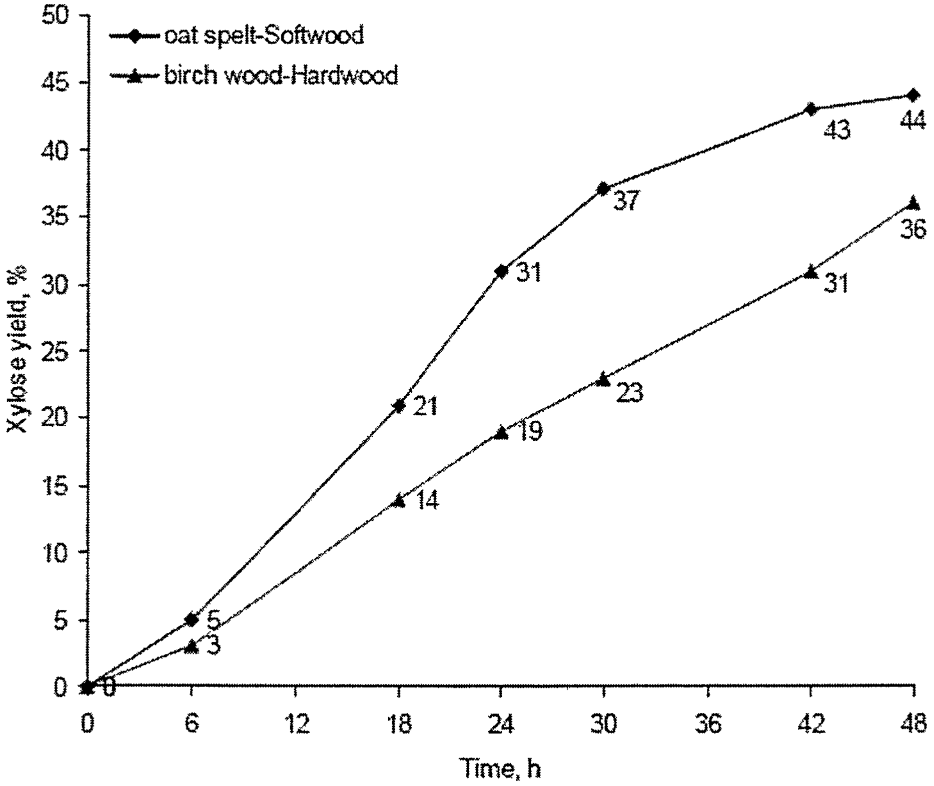
FIG. 5 illustrates effect of hemicellulose source on hydrolysis: Xylan (oat spelt or birch wood), 0.6 g; HUSY (Si/Al=15), 0.3 g; water, 60 g; $N_2$ pressure, 50 bar at RT; temperature, 130° C.; reaction time, 48 h; stirring, 500 rpm.

It is well known that softwood and hardwood derived hemicelluloses have different morphology and that the Degree of Polymerization (DP) i.e. total Xylose units linked with each other to form a polymer are different. In case of softwood hemicellulose, it is reported that DP is approximately 100 while for hardwood hemicellulose it is around 200. This makes the hardwood hemicellulose difficult to degrade or may be the rate of reaction is lower. Considering this, study on hemicellulose source was carried out and results are presented in FIG. 5. It is observed that almost same xylose formation is possible with any hemicelluloses substrate.

It is observed that with solid acid catalysts hemicellulose is hydrolyzed to monosaccharides such as xylose, glucose, arabinose, mannose, oligomers such as xylopentaose, xylotetraose, xylotriose, xylobiose and is also being further converted into furaldehyde and 5-hydroxymethyl furfuraldehyde (HMF). The xylose derived can be widely used as a raw material for the synthesis of variety of chemicals either chemically or biochemically. xylitol production after hydrogenation of —CHO group from xylose is well reported. Further, xylitol is extensively used in food, pharmaceutical and thin coating applications. The more important use of xylitol is as a sweetener and is used in sugar-free sweets; that can be consumed by diabetic patients. Xylose can also be converted into glycols (ethylene, propylene etc.) and can also act as hydrogen source as shown for sorbitol substrate. The xylose can also be converted into ethanol, 2,3-butanediol, lactic acid and many other chemicals.

The process of the invention has the following advantages over conventional mineral acid (HCl, $H_2SO_4$) catalyzed and enzyme catalyzed processes:

1. It is a non-corrosive system.
2. The process does not generate any neutralization waste as system operates at neutral pH due to solid acid catalyst and water is used as a reaction media.
3. Separation of catalyst and product is easy, as the catalyst is solid and insoluble in reaction media while products (xylose arabinose, glucose, furaldehyde, oligomers etc.) formed are soluble in water. Hence the overall costly process of separation of catalyst from reaction media/product is avoided and just simple filtration step can be employed.

4. Handling of catalyst is very easy and does not need any special precaution as required for handling mineral acids.
5. The reaction is industrially applicable.

The process of the present invention is described herein below with reference to the following examples, which are illustrative only and should not be construed to limit the scope of the invention in any manner.

Example 1

In an autoclave 0.6 g xylan (hemicellulose derived from softwood oat spelt), 0.3 g HUSY (Si/Al=15) and 60 g of water are charged. Reactor is flushed 3 times with nitrogen gas.

After this 50 bar nitrogen is charged in the reactor. Reactor is heated up to 130° C. under low stirring (100 rpm). Upon attaining the desired temperature of 130° C. stirring was increased up to 500 rpm. Periodic sampling was done and reaction was stopped after 48 hours.

Analysis of Reaction Mixture:

Reaction mixture is analyzed by HPLC (Shimadzu co., Japan). Water is used as an eluting solvent. UV-vis and Refractive Index detector (RID) are used for the detection of compounds. The calibration of all the compounds (Xylose, arabinose, glucose, 5-hydroxy methyl furfural (HMF) and furaldehyde) was performed prior to analysis. Confirmation of products was also done by LC-MS analysis.

Example 2

In an autoclave (batch reactor), 0.6 g xylan (hemicelluloses derived from softwood, oat spelt), 0.3 g $Cs_{2.5}H_{0.5}PW_{12}O_{40}$ and 60 g of water are charged. Reactor is flushed 3 times with nitrogen gas. After this 50 bar nitrogen is charged in the reactor. Reactor is heated up to 130° C. under the low stirring (100 rpm). Upon attending the desired temperature of 130° C. stirring was increased up to 500 rpm. Periodic sampling was done and reaction was stopped after 24 hours to yield 40% xylose.

Example 3

In an autoclave, 0.6 g xylan (hemicelluloses derived from softwood, oat spelt), 0.3 g HUSY (Si/Al=15) and 60 g of water are charged. Reactor is flushed 3 times with helium gas. After this 50 bar helium is charged in the reactor. Reactor is heated up to 130° C. under the low stirring (100 rpm). Upon attending the desired temperature of 130° C. stirring is increased up to 500 rpm. Periodic sampling is done and reaction is stopped after 48 hours to yield 38% xylose.

Example 4

In an autoclave, 0.6 g xylan (hemicelluloses derived from softwood, oat spelt), 0.3 g $Nb_2O_5$ and 60 g of water are charged. Reactor is flushed 3 times with nitrogen gas. After this 50 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 3 hours to yield 19% xylose.

Example 5

In an autoclave, 0.6 g xylan (hemicelluloses derived from softwood, oat spelt), 0.3 g $Al_2O_3$ and 60 g of water are charged. Reactor is flushed 3 times with nitrogen gas. After this 50 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 3 hours to yield 20% xylose.

Example 6

In an autoclave, 0.6 g xylan (hemicelluloses derived from softwood, oat spelt), 0.3 g $SO_4^{2-}/ZrO_2$, 60 g of water and 50 bar argon are charged. Reactor is heated up to 170° C. under the low stirring (100 rpm). Upon attending the desired temperature of 170° C. stirring is increased up to 500 rpm. Reaction was stopped after 3 hours. (No flushing is done) to yield 11% xylose.

Example 7

In an autoclave, 0.6 g xylan (hemicelluloses derived from softwood, oat spelt), 0.3 g Al-MCM-41 (Si/Al=50) and 60 g of water are charged. Reactor is flushed 3 times with nitrogen gas. After this 50 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 3 hours to yield 14% xylose.

Example 8

In an autoclave, 0.6 g xylan (hemicelluloses derived from softwood, oat spelt), 0.3 g Al-SBA-15 (Si/Al=10) and 60 g of water are charged. Reactor is flushed 3 times with nitrogen gas. After this 50 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 3 hours to yield 4% xylose.

Example 9

In an autoclave, 0.6 g xylan (hemicelluloses derived from softwood, oat spelt), 0.3 g Amberlyst-15 (catalyst is water refluxed and washed with hot water prior to use) and 60 g of water are charged. Reactor is flushed 3 times with nitrogen gas. After this 50 bar nitrogen is charged in the reactor. Reactor is heated up to 130° C. under the low stirring (100 rpm). Upon attending the desired temperature of 130° C. stirring is increased up to 500 rpm. Periodic sampling is done and reaction is stopped after 48 hours to yield 7% xylose.

Example 10

In an autoclave, 0.6 g xylan (hemicelluloses derived from softwood, oat spelt), 0.3 g $SiO_2Al_2O_3$ (Si/Al=15) and 60 g of water are charged. Reactor is flushed 3 times with nitrogen gas. After this 50 bar nitrogen is charged in the reactor. Reactor is heated up to 130° C. under the low stirring (100 rpm). Upon attending the desired temperature of 130° C. stirring is increased up to 500 rpm. Periodic sampling is done and reaction is stopped after 24 hours to yield 5% xylose.

Example 11

In an autoclave, 0.6 g xylan (hemicelluloses derived from softwood, oat spelt), 0.3 g Ga-MCM-41 (Si/Ga=10) and 60 g of water are charged. Reactor is flushed 3 times with nitrogen gas. After this 50 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 3 hours to yield 9% xylose.

Example 12

In an autoclave, 0.6 g xylan (hemicelluloses derived from softwood, oat spelt), 0.01 g HUSY (Si/Al=15) and 60 g of water are charged. Reactor is flushed 3 times with nitrogen gas. After this 50 bar nitrogen is charged in the reactor. Reactor is heated up to 130° C. under the low stirring (100 rpm). Upon attending the desired temperature of 130° C. stirring is increased up to 500 rpm. Periodic sampling is done and reaction is stopped after 48 hours to yield 34% xylose.

Example 13

In an autoclave, 0.6 g xylan (hemicelluloses derived from softwood, oat spelt), 0.3 g HUSY (Si/Al=15) and 20 g of water are charged. Reactor is flushed 3 times with nitrogen gas. After this 50 bar nitrogen is charged in the reactor. Reactor is heated up to 130° C. under the low stirring (100 rpm). Upon attending the desired temperature of 130° C. stirring is increased up to 500 rpm. Periodic sampling is done and reaction is stopped after 24 hours to yield 36% xylose.

Example 14

In an autoclave, 0.6 g xylan (hemicelluloses derived from softwood, oat spelt), 0.3 g HUSY (Si/Al=15) and 60 g of solvent (40 g toluene and 20 g water) are charged. Reactor is flushed 3 times with nitrogen gas. After this 50 bar nitrogen is charged in the reactor. Reactor is heated up to 120° C. under the low stirring (100 rpm). Upon attending the desired temperature of 120° C. stirring is increased up to 1000 rpm. Periodic sampling is done and reaction is stopped after 48 hours to yield 8% xylose.

Example 15

In an autoclave, 0.6 g xylan (hemicelluloses derived from softwood, oat spelt), 0.3 g HUSY (Si/Al=15) and 60 g of water are charged. Reactor is flushed 3 times with nitrogen gas. After this 50 bar nitrogen is charged in the reactor. Reactor is heated up to 130° C. under the low stirring (100 rpm). Upon attending the desired temperature of 130° C. stirring is increased up to 1000 rpm. Periodic sampling is done and reaction is stopped after 48 hours to yield 42% xylose.

Example 16

In an autoclave (batch reactor), 0.6 g xylan (hemicelluloses derived from softwood oat spelt), 0.3 g HUSY (Si/Al=15) and 60 g of water are charged. Reactor is heated up to 130° C. under the low stirring (100 rpm). Upon attending the desired temperature of 130° C. stirring is increased up to 500 rpm. Periodic sampling is done and reaction was stopped after 48 hours. In this reaction no inert gas is used and it yielded 38% xylose.

Example 17

In an autoclave (batch reactor), 0.6 g xylan (hemicelluloses derived from softwood oat spelt), 0.3 g sulfonated MCM-41 (MCM-41 with —$SO_3H$ group attached) and 60 g of water are charged. Reactor is flushed 3 times with nitrogen gas and 50 bar nitrogen is charged in the reactor. Reactor is heated up to 120° C. under the low stirring (100 rpm). Upon attending the desired temperature of 120° C. stirring is increased up to 500 rpm. Periodic sampling is done and reaction is stopped after 48 hours to yield 10% xylose.

Example 18

In an autoclave, 0.6 g xylan (hemicelluloses derived from softwood oat spelt), 0.3 g montmorillonite K10 (clay) and 60 g of water are charged. Reactor is flushed 3 times with nitrogen gas and 50 bar nitrogen is charged in the reactor. Reactor is heated up to 170° C. under the low stirring (100 rpm). Upon attending the desired temperature of 170° C. stirring is increased up to 500 rpm. Periodic sampling was done and reaction is stopped after 3 hours. This resulted in 29% yield of xylose.

Example 19

In an autoclave (batch reactor), 0.6 g xylan (hemicelluloses derived from softwood, oat spelt), 0.6 g HUSY (Si/Al=15) and 60 g of water are charged. Reactor is flushed 3 times with nitrogen gas and 50 bar nitrogen is charged in the reactor. Reactor is heated up to 170° C. under the low stirring (100 rpm). Upon attending the desired temperature of 170° C. stirring is increased up to 500 rpm. Periodic sampling was done and reaction is stopped after 3 hours.

After removing the reaction mixture from autoclave, it is centrifuged and wet powder (containing catalyst and unreacted hemicellulose) is removed. This wet powder is washed 3 times by cold distilled water. Next, powder is used for next reaction with charge as follows, 0.6 g xylan, recovered HUSY (Si/Al=15) catalyst with unreacted hemicellulose (wet powder) and 60 g of water. The reaction conditions for recycle experiment are same as above. Periodic sampling is done and reaction was stopped after 3 hours, resulting in 36% xylose yield.

Example 20

In a teflon reactor (batch reactor), 0.4 g xylan (hemicelluloses derived from softwood oat spelt), 0.2 g HUSY (Si/Al=15) and 40 g of water are charged. Reactor is heated up to 130° C. under the stirring (rpm is not measured). Reaction is stopped after 24 hours, to yield 30% xylose.

Example 21

In an autoclave (batch reactor), 0.6 g xylan (hemicelluloses derived from softwood oat spelt), 0.24 g HUSY (Si/Al=15) & 0.06 g $SO_4^{-2}/ZrO_2$ (total catalyst amount, 0.3 g) and 60 g of water are charged. Reactor is flushed 3 times with nitrogen gas. After this 50 bar nitrogen is charged in the reactor. Next, reactor is heated up to 170° C. under the low stirring (100 rpm). Upon attending the desired temperature of 170° C. stirring is increased up to 500 rpm. Periodic sampling is done and reaction is stopped after 3 hours to obtain 33% yield of xylose.

Example 22

In an autoclave (batch reactor), 0.6 g xylan (hemicellulose derived from hardwood birchwood), 0.3 g HUSY (Si/Al=15) and 60 g of water are charged. Reactor is flushed 3 times with nitrogen gas. After this 50 bar nitrogen is charged in the reactor. Next, reactor is heated up to 130° C. under the low stirring (100 rpm). Upon attending the desired temperature of 130° C. stirring is increased up to 500 rpm. Periodic sampling is done and reaction was stopped after 48 hours. The result of the reaction is 36% xylose yield.

Example 23

In an autoclave, 0.6 g bagasse, 0.3 g HUSY (Si/Al=15) and 60 g of water are charged. Reactor is flushed 3 times with nitrogen gas. After this 50 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 1.5 hours to yield 0.09 g xylose.

Example 24

In an autoclave, 0.6 g bagasse, 0.3 g montmorillonite K10 (clay) and 60 g of water are charged. Reactor is flushed 3 times with nitrogen gas. After this 50 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 1.5 hours to yield 0.08 g xylose.

Example 25

In an autoclave, 0.6 g bagasse, 0.3 g HBeta (Si/Al=19) and 60 g of water are charged. Reactor is flushed 3 times with nitrogen gas. After this 50 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 2 hours to yield 0.09 g xylose.

Example 26

In an autoclave, 0.6 g bagasse, 0.3 g HUSY (Si/Al=15) and 60 g of water are charged. Reactor is flushed 3 times with nitrogen gas. After this 50 bar nitrogen is charged in the reactor. Reactor is heated up to 120° C. under the low stirring (100 rpm). Upon attending the desired temperature of 120° C. stirring is increased up to 500 rpm. Periodic sampling is done and reaction is stopped after 40 hours to yield 0.08 g xylose.

Example 27

In an autoclave, 0.6 g bagasse, 0.3 g HUSY (Si/Al=15) and 60 g of water are charged. Reactor is flushed 3 times with nitrogen gas. After this 50 bar nitrogen is charged in the reactor. Reactor is heated up to 140° C. under the low stirring (100 rpm). Upon attending the desired temperature of 140° C. stirring is increased up to 500 rpm. Periodic sampling is done and reaction is stopped after 12 hours to yield 0.08 g xylose.

Example 28

In an autoclave, 0.6 g bagasse, 0.3 g HUSY (Si/Al=15) and 60 g of water are charged. Reactor is flushed 3 times with nitrogen gas. After this 1 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 1.5 hours to yield 0.08 g xylose.

Example 29

In an autoclave, 0.6 g bagasse, 0.3 g HUSY (Si/Al=15) and 60 g of water are charged. Reactor is flushed 3 times with nitrogen gas. After this 5 bar nitrogen is charged in the reactor. Reactor is heated up to 170° C. under the low stirring (100 rpm). Upon attending the desired temperature of 170° C. stirring is increased up to 500 rpm. Periodic sampling is done and reaction is stopped after 1.5 hours to yield 0.09 g xylose.

Example 30

In an autoclave, 0.6 g bagasse, 0.3 g HUSY (Si/Al=15) and 60 g of water are charged. Reactor is flushed 3 times with nitrogen gas and 50 bar nitrogen is charged in the reactor. Reactor is heated up to 170° C. under the low stirring (100 rpm). Upon attending the desired temperature of 170° C. stirring is increased up to 500 rpm. Periodic sampling was done and reaction is stopped after 2 hours to yield 0.09 g xylose.

After removing the reaction mixture from autoclave, it is centrifuged and wet powder (containing catalyst and unreacted bagasse) is removed. This wet powder is washed 3 times by cold distilled water. Next, powder is used for next reaction with charge as follows, 0.6 g bagasse, recovered HUSY (Si/Al=15) catalyst with unreacted bagasse (wet powder) and 60 g of water. The reaction conditions for recycle experiment are same as above. Periodic sampling is done and reaction was stopped after 2 hours, resulting in 0.08 g xylose.

Example 31

Lignocellulosic material (Bagasse) (0.6 g) without any physical and/or chemical pre-treatment was mixed with water (30 g), toluene (30 g) and solid acid catalyst, 0.3 g in an autoclave. Reaction temperature of 170 degc was maintained without N2 pressure. Furfural yield of 40% was observed with HUSY (Si/Al=15) catalyst after 5 h reaction time.

Example 32

Lignocellulosic material (Bagasse) (0.6 g) without any physical and/or chemical pre-treatment was mixed with water (30 g), toluene (30 g) and solid acid catalyst, 0.3 g in an autoclave. Reaction temperature of 170 degc was maintained with either N2 pressure (5 bar). Furfural yield of 40% was observed with HUSY (Si/Al=15) catalyst after 5 h reaction time.

We claim:

1. One pot and single step hydrolytic process for the conversion of lignocellulosic xylan to value added derivative products selected from the group consisting of xylose and arabinose wherein said process comprises:

a. charging the xylan in a reactor followed by charging a solvent and at least one heterogeneous solid acid catalyst;

b. adjusting the pressure to 1-70 bar and temperature in the range of 50-250° C. of the reactor, under stirring;

c. raising the stirring speed to 10-2000 rpm after stabilizing the temperature of the reactor in the range 50-250° C.; and d. carrying the above said reaction for a period of 0.1 to 96 hours to obtain said value added derivative product wherein said heterogeneous solid acid catalyst is selected from the group consisting of HUSY™ (Si/Al=15), Cs0.25H0.5PW12040, Nb205, Al203, SO42-/ZRO2, A1-MCM-41 (Si/Al=50), A1-SBA-15 (Si/Al=10), an ion exchange resin sold under the trademark Amberlyst-15, SiO2-Al03 (Si/A1=15), Ga-MCM-41, sulfonated MCM-41, and Montmorillonite K10 (clay).

2. The process as claimed in claim 1, wherein i) said process comprises a step of flushing the reactor with inert gas or air after step (a) and before step b wherein said inert gas is selected from the group consisting of nitrogen, argon, helium and hydrogen; and ii) the xylan to solvent ratio is in the range 0.001-0.5 wt/wt; or the xylan to catalyst ratio is in the range 0.2-500 wt/wt.

3. A process as claimed in claim 1, wherein the solvent in the reaction is optionally organic solvent or a mixture of water and organic solvent in a ratio of 1:99 to 99:1 and said organic solvent is selected from the group consisting of alcohols, ethers, esters, hexane, acids, toluene, and xylene.

* * * * *